US006485752B1

(12) United States Patent
Rein

(10) Patent No.: US 6,485,752 B1
(45) Date of Patent: Nov. 26, 2002

(54) COMPOSITION AND METHOD FOR ALLEVIATING JOINT PAIN AND STIFFNESS

(75) Inventor: Eydbjørg Rein, Randbøl (DK)

(73) Assignees: Otto Torbjorn Hansen, Tullebolle (DK); Marianne Hansen, Tullebolle (DK)

( * ) Notice: Subject to any disclaimer, the term of this patent is extended or adjusted under 35 U.S.C. 154(b) by 0 days.

(21) Appl. No.: 09/694,764

(22) Filed: Oct. 23, 2000

(51) Int. Cl.[7] .................... A61K 35/60; A61K 35/78; A01N 25/00
(52) U.S. Cl. .................. 424/523; 424/725; 424/765; 514/824; 514/825
(58) Field of Search ............................. 424/523, 725, 424/765; 514/825, 824

(56) References Cited

U.S. PATENT DOCUMENTS

| | | |
|---|---|---|
| 4,565,690 A | 1/1986 | Revici |
| 4,774,229 A | 9/1988 | Jordan |
| 4,839,172 A * | 6/1989 | Morishige .................... 424/105 |
| 5,032,400 A * | 7/1991 | Wiersum et al. .......... 424/195.1 |
| 5,431,924 A * | 7/1995 | Ghosh et al. ................ 424/522 |
| 5,585,118 A | 12/1996 | Stoll |
| 5,595,743 A | 1/1997 | Wu |
| 5,744,187 A | 4/1998 | Gaynor |
| 6,024,960 A | 2/2000 | Kharazmi et al. |

FOREIGN PATENT DOCUMENTS

EP 0861662 A1 2/1998

OTHER PUBLICATIONS

"The anti-inflammatory properties of rose-hip," Inflammopharmacology, vol. 7, No. 1, pp. 63–69 (1999), K. Winther, E. Rein and A. Karazmi.
CA 104: 17649, F. Morishigel, Nissan Chemical Industries Ltd., Japan, Dec. 11, 1985.
CA 101: 136, B. Spilker et. al., Curr. Ther. Res. 1984 (34) (4) 593–605.
Fabad. J. Pharm. Sci. 15, 121–131, 1990, S. Kurucu et. al. "Rose hip inhibits chemotaxis and chemiluminescence of human peripheral blood neutrophils. . ." Inflammopharmacology, vol. 7, No. 4, pp. 377–386 (1999), A. Kharazmi and K. Winther.
"Cardiovascular Effects of n–3 Fatty Acids," Medical Progress, The New England Journal of Medicine, vol. 318, No. 9, (Mar. 3, 1988) A. Leaf and P. Weber.
"Validation of a Meta–Analysis: The Effects of Fish Oil in Rheumatoid Arthritis," J. Clin Epidemiol vol;. 48, No. 11, pp. 1379–1390, (1995), P. Fortin et al.
"Hyben Vital, a Herbal Remedy, Reduces Pain and Stiffness. . . ," O. Warholm et al., Beijing 9th Aplar Congress, China 2000.
"Rose–Hip Given as a Standardised Dry Powder. . . ," Abstract Form, 2nd Int. Congress on Coronary Artey Disease, (Oct. 18, 1998–Oct. 21, 1998), Florence, Italy, K. Winther et. al.
"Rose–Hip Given as a Standardised Dry Powder . . . ," Abstract Form, 1st Int. Congress on Heart Disease, (May 16, 1999–May 19, 1999), Washington D.C., E. Rein et. al.
Abstract, PCT WO/99 53934 (Cumulative to U.S. Patent No. 6024960).
Usefulness of fish oil supplements. . . , A.M.J. Cardiol. 64, No. 5, 2 94–99, 1989 Milner et. al.

* cited by examiner

Primary Examiner—Christopher R. Tate
Assistant Examiner—Kailash C. Srivastava
(74) Attorney, Agent, or Firm—William J. Sapone; Coleman Sudol Sapone, P.C.

(57) ABSTRACT

A daily administration of a rose-hip concentrate and fish oil is used to treat and/or alleviate the symptoms associated with joint disease such as osteoarthritis, specifically joint pain and stiffness. By administering the combination on a daily basis, a significant reduction in pain and stiffness of the joints affected by joint disease is attained which allows individuals suffering from joint disease to substantially resume daily activities.

11 Claims, No Drawings

COMPOSITION AND METHOD FOR ALLEVIATING JOINT PAIN AND STIFFNESS

TECHNICAL FIELD

This invention relates to the use of a composition containing a rose hip extract and fish oil for the treatment of pain and stiffness in the joints, such as associated with osteoarthritis.

BACKGROUND

Various rose hip formulations are known. For example, in U.S. Pat. No. 6,024,960, commonly assigned with the present application, a rose hip formulation for use as an anti-inflammatory natural medicine is described.

Fish oil is also a known material that has some beneficial effects. In particular, the n-3 polyunsaturated fatty acids (n-3 PUFA) of dietary fish oil are known to reduce the level of triglycerides and very low density lipoprotein cholesterol. Dietary supplementation by, for example, 1.0 ml capsules of fish oil containing about 0.3 g of the primary n-3 PUFA, eicosapentaenoic acid (EPA) and docosahexanoic acid (DHA), have been used, though other concentrations of the PUFA's in supplements are available, ranging for example from 20 to 50% by weight.

Osteoarthritis is characterized by an erosion of articulated cartilage which becomes soft, frayed and thinned with eburnation of subchcondral bone and outgrowths of marginal osteophytes. Pain and loss of function result. This is more common in older persons and is considered a degenerative joint disease which mainly affects the weight bearing joints such as the hips and knees.

While inflammation is one symptom of arthritis, the pain and stiffness of the joints is particularly debilitating as this physically inhibits activity and lessens the motivation for daily activities, as well as causing sleeplessness, and results in an overall negative impact on the general well being of an individual, as one susceptible to such pain and joint stiffening must generally refrain from normal daily activities such as walking, entering a vehicle, etc.

SUMMARY OF THE INVENTION

It is an object of the present invention to provide a formulation for the treatment of symptoms associated with joint disease.

It is a further object of the present invention to provide a formulation for the prophylaxis of joint disease.

It is a further object of the present invention to provide a formulation based on natural products to substantially avoid side effects associated with traditional drugs used to treat joint pain and stiffness.

It is yet another object to provide a method for treating and alleviating the symptoms of pain and joint stiffness associated with joint disease.

These and other objects of the present invention are achieved by a combination of a rose hip concentrate and fish oil, preferably in a physiologically acceptable carrier. Using the combination, a surprising improvement in pain relief and reduction in joint stiffness is achieved with a consequent improvement in overall well being.

DETAILED DESCRIPTION OF THE INVENTION

The present invention is directed to a formulation using natural ingredients in the treatment of the symptoms associated with joint disease, particularly joint pain and joint stiffness. The formulation includes two primary ingredients, a rose hip extract and fish oil containing n-3 PUFA's.

As these are natural substances, their exact composition may vary somewhat. The rose hip component may be an extract (also referred to herein as a "concentrate") generally having a high vitamin C content, in the range of about 0.6 to 1.5 mg per g, as well as other vitamins and minerals. Preferably, a rose hip extract produced in accordance with the description in U.S. Pat. No. 6,024,960 is used as that extract is obtained by a process that substantially preserves the vitamin content. Of course, the quantities of the specific vitamins and minerals may vary by species or through use of different extraction/concentration methods. An exemplary rose hip extract in powder form is shown in Table I, though the invention is not limited thereto.

TABLE 1

| Analysis (per 400 g) | Result |
|---|---|
| Vitamin A | <10 µg/100 g |
| Vitamin B1 | <0.2 mg/100 g |
| Vitamin B2 | 0.99 mg/100 g |
| Vitamin B6 | 0.20 mg/100 g |
| Vitamin B12 | <0.5 µg/100 g |
| Vitamin C | 560 mg/100 g |
| Vitamin K1 | 63 µg/100 g |
| Vitamin E | 4.6 mg/100 g |
| Niacin | 0.96 mg/100 g |
| Calcium | 630 mg/100 g |
| Phosphorus | 160 mg/100 g |
| Magnesium | 170 mg/100 g |
| Iron | 1.9 mg/100 g |
| Potassium | 0.97% |
| Sodium | 0.018% |
| Sulphur | 1000 mg/kg |
| Zinc | 1.0 mg/100 g |
| Copper | 10,900 µ100 g |
| Manganese | 3,900 µg/100 g |
| Silicon | 85 mg/kg |
| Iodine | 93 µg/100 g |
| Selenium total | <0.020 mg/kg |
| Chromium | <0.020 mg/kg |
| Molybdenum | 0.21 mg/kg |
| Cobalt | <0.050 mg/kg |
| Nickel | 0.79 mg/kg |
| Aluminum | 8.7 mg/kg |
| Boron | 15 mg/kg |
| Fluorine | 2 mg(kg |
| Chloride | 0.5 g/kg |
| Lithium | 0.041 mg/kg |

Preferably, the rose hip extract is in powdered form and can be pelletized or placed in capsules with a physiologically acceptable carrier for formulation into unit dosages. A unit dosage comprises a therapeutically effective daily amount of the rose hip which can be taken as a single daily administration or by multiple small doses taken over the course of a day. In either instance, the formulation can be manufactured into tablets, capsules, caplets, elixirs, enteral formulations or be incorporated into slow release carriers. Examples of physiologically acceptable carriers would include water, oil emulsions, alcohol, etc.

A unit dosage may vary based upon many factors such as age, condition and disease state of the individual and number of times the units may be taken in a single day. In any event, the entire daily dosage will be that which is physiologically acceptable and tolerable to an individual and which can be administered daily for a long period of time, as joint disease is a chronic illness.

A preferred unit dosage of the rose hip ingredient will be from about 0.02 to about 0.3 g/kg per day or about 1.5 to 30 g per day. About 2.5 to 15 g per day are preferred, and about 2.5 to 6.0 g are most preferred.

The fish oil ingredient, also as a natural substance, may vary in its concentration of n–3 PUFAX's. Thus, the amount constituting a unit dose may vary in relation to the concentration of the fatty acids. For example, fish oil may contain from 1 to 50% by weight of the n–3 PUFA's, particularly, eicosapentaenoic acid and docosahexanoic acid, typically measured as triglycerides. The lower the concentration of n–3 PUFA's, the higher unit daily dosage should be administered, i.e., five capsules at 10% would be equivalent to one capsule at 50%.

This can, of course, vary with the type of fish used to obtain the fish oil and the processing used to produce the fish oil component, which techniques are conventional in the art. For example, cod fish oil may have about 20% of the n–3 PUFA's while other species may have more or less and this amount may be further concentrated using appropriate conventional processing steps. The most common fish oil supplement is in the form of 1.0 ml capsules, containing about 0.3 g of PUFA's per capsule, though capsules containing up to 50% PUFA's are commercially available.

The fish oil may be obtained in a dry powdered form. For example, a dry powder containing 25% by weight of fish oil is commercially available, one such powder containing 25.7% n–3 18:22 fish oil, having from about 41.0 to 42.2 mg/g EPA as triglycerides and from about 27.0 to 28.8 mg/g DHA calculated as triglycerides. Such a material is well suited for use in accordance with the present invention.

A unit daily dose of fish oil in accordance with the present invention should be in the range of about 500–3600, more preferably 1300–2600 mg of the n–3 PUFA containing fish oil per day in either a single dose or in multiple smaller doses, so as to provide from about 0.1 to 1.8 g PUFA's per day, more preferably about 0.1 to 0.8 g PUFA's per day.

Of course, the ingredients can be preferably combined and formulated together, though separate administration is possible so as to distribute the consumption of these ingredients over the course of a day.

Another way to characterize the inventive formulation is by ratio. The ratio of rose-hip concentrate to fish oil may vary from about 20 to 1 to about 1.3 to 1, with a preferred ratio being about 5 to 1 to 1.6 to 1, g rose-hip to g fish oil. For example, multiple capsules having the exemplary ratio of ingredients may be prepared, so as to allow the daily dosage to be taken proportionally over the course of the day.

The following examples describe the present invention in more detail though the invention is not limited to the specific details cited therein.

Fish Oil Compared to Fish Oil and Rose-hip

Fifty-four patients all suffering from X-ray verified osteoarthrosis and all on a waiting list for hip or knee surgery and who had been taking fish oil (n–3 PUFA) 2–4 capsules (1.3–2.6 g) daily for at least the previous year were randomly allocated to either Rose-hip capsules, 5 g daily (n=29) or identical placebo capsules (n=25) for a four month treatment period. During the entire four month treatment period the intake of fish oil was kept unchanged. The two groups were comparable as to age, sex, social class, degree of osteoarthrosis and fish consumption through their daily diet. The following data are all evaluated using the Wilcoxon test for matched pairs.

At start and after four months of treatment, stiffness of the hip and/or knee was estimated using a visual analogue scale.

During treatment with the combination fish oil and Rose-hip, stiffness declined from 11.48+/−4.56 to 8.21+/−5.07 (p<0.001).

For those taking fish oil and placebo, stiffness declined from 11.00 +/−5.57 to 9.36 +/−5.46 (p<0.124, not significant).

At start and after four months of therapy, difficulties performing daily activities such as climbing stairs, standing up from a chair, walking on the street, entering a car or bus, going shopping, pulling on stockings, performing daily household chores, etc. was estimated using visual analogue scales. At the end, all scales were added together.

In the group receiving fish oil and Rose-hip the score declined from 74.21+/−29.23 to 59.62+/−38.79 (p<0.015). For those taking fish oil and placebo, the score declined a less significant amount from 72.00+/−25.52 to 63.28+/−33.38 (p<0.228).

The volunteers were asked to evaluate the severity of their arthrosis at start and after four weeks of therapy. During the combination therapy, there was a decline in score from 5.79+/−2.06 to 4.86+/−2.61 (p<0.043). The combination of fish oil and placebo resulted in a much smaller and insignificant decline as shown by the fall from 6.00 +/−2.58 to 5.68+/−2.84 (p).

Flexion of the hip and knee (the ability to bend the hip and knee), before and after four months of therapy, resulted in a significant improvement for those taking the combination. Those on Rose-hip and fish oil saw the degree of flexion increase from 126.21+/−15.10 degrees to 129.31+/−15.28, an improvement of more than 3 degrees (p<0.002). In the group receiving fish oil and placebo, there was no significant change from 123.80+/−16.35 to 124.80+/−16.30 (p<0.304).

Pain, energy, general well-being, motivation for daily activities and sleep were measured using a simple questionnaire asking Yes or No for improvement. This test was performed after one, two and four months of treatment. All yes answers in each of the two groups, fish oil +Rose-hip and fish oil +placebo were recorded and the CHI-square test was used for statistical evaluation.

The group receiving fish oil and Rose-hip significantly declined in pain after only one month of treatment as compared to fish oil and placebo (p<0.019). The impact on pain remained constant during the whole study period. The energy score also improved after one month on the combination therapy (p<0.01) and remained significant during the rest of the trial.

Likewise the feeling of general well-being significantly increased while on the combination therapy (p<0.03). The improvement was significant after one month of treatment and remained stable during the rest of the four month treatment period.

Motivation for daily activities also improved after one month of treatment while on fish oil combined with Rose-hip as compared to fish oil and placebo (p<0.03). After 4 months of treatment the p level was still <0.03).

In agreement with the findings presented above, sleep improved as a result of the combination therapy (p<0.017). This improvement was still significant after 4 months of therapy (p<0.035). Placebo and fish oil did not in any single case result in any significant or borderline-significant value.

Rose-hip Compared to Fish Oil and Rose-hip

Forty eight patients all suffering from X-ray verified osteoarthrosis and all on a waiting list for hip or knee surgery, received Rose-hip 5 grams daily for a four month period. Of these, 29 in addition received fish oil, (n–3 PUFA) 2–4 capsules (1.3–2.6 g) daily for the fall four month period. The remaining 29 did not receive any type of fish oil supplement. The two groups were comparable regarding age, sex, degree of osteoarthrosis and fish consumption through their daily diet.

When pain was evaluated on a scale from 0 (no effect) to 4 (total relief of pain), the pain score was significantly declined in the group receiving rose-hip and fish oil as compared to the group receiving rose-hip alone(p<0.005) Mann-Whitney.

In agreement with the decline in pain score, stiffness of the joints significantly declined when evaluated on a visual analogue scale in the group receiving the combination of rose-hip and fish oil. The initial value was 11.48+/−3.56 which declined to 8.21+/−5.07(p<0.0012) Wilcoxon. In the group receiving rose-hip only, the initial value was 10.68+/−5.35. After four months of therapy, the value was 10.26+/−5.34 (not significant).

An index showing the ability to perform daily activities such as shopping, entering a car, or bus, climbing stairs, house cleaning, gardening, etc., estimated on a visual analogue scale showed a highly significant improvement in the group receiving the combination fish oil and rose-hip. The mean value declined from 74.21+/−29.23 to 59.62+/−38.79, (p<0.015) Wilcoxon. In the group receiving rose-hip alone, there was only a decline from 77.95+/−36.65 to 70.58+/−43.52 (not significant).

In accordance with these findings, an overall evaluation of the total impact of treatment on the disease evaluated on a visual analogue scale came out in favor of the combination treatment, which resulted in a decline from 5.79+/−2.06 to 4.86+/−2.61 (p<0.043). Rose-hip alone did not change the overall evaluation as shown by a decline from 5.79+/−2.66 to 5.42+/−2.43 (not significant).

Energy, general well being, motivation for daily activities and quality of sleep were estimated on a simple questionnaire asking yes or no for improvement. This test was made after one month and four months of therapy.

In the group receiving the combination rose hip and fish oil, energy improved significantly after one month(p<0.01) and four months (p<0.047) CHI square. In the group receiving Rose-hip alone, there was a similar trend but not a significant improvement. .

General well being improved significantly after one month (p<0.03) and four months (p<0.03) while on the combination. Rose hip alone showed a similar trend but not in a significant amount.

Likewise, motivation for daily activities improved significantly as shown by a p value <0.036 after one month and a p value <0.022 after four months. Again, on Rose-hip alone, though there was improved motivation, there was no significant change.

Finally, the quality of sleep significantly improved after one month (p<0.017) and after four months (p<0.035), while on rose hip alone, no significant improvement was observed.

This test showed that the combination of rose hip and fish oil is superior to rose hip alone, in alleviating pain and stiffness of the hip and knee. In addition, energy, general well being, motivation for daily activities and sleep improved while on the combination.

While it was recognized that fish oil to some extent reduced pain and stiffness in patients with joint disease, the salient finding is that Rose-hip combined with fish oil is proven to alleviate pain and stiffness of the hip and knee, much better than fish oil combined with placebo or Rose-hip alone. Rose-hip significantly adds to the beneficial effect of fish oil on stiffness and pain of the hip and knee. This additive effect is new and has never been described before. In addition the combination of fish oil and Rose-hip improves energy, general well being, motivation for daily activities and sleep when compared to fish oil and placebo and finally the combination also significantly reduces pain. This also is a new unexpected finding never described before.

The present data indicate that the combination of rose-hip and fish oil is superior to fish oil alone regarding alleviation of pain and stiffness of the hip and knee. In addition, energy, general well-being, motivation for daily activities and sleep improved while on the combination.

While it is not completely clear as to why the combination achieves such superior results at such relatively low doses, it is believed that arachidonic acid in the membranes of different cell types may be a key in the production of eicosanoids such as prostaglandin, thromboxane and leucrotriene which are all essential in the development of cell injury and pain in diseases including rheumatoid arthritis and osteoarthrosis.

Intake of fish oil rich in n–3 PUFA's is believed to result in a decrease in cell membrane arachidonic acid level and a concomitant decrease in the synthesis of eicosanoids (prostaglandins, thromboxanes and leucotriens) from arachidonic acid.

One of the mechanisms behind rheumatoid and osteoarthritic pain and stiffness, is a liberation of cytotoxic agents from neutrophils, which results in destruction of tissue and the formation of oedema, resulting in pain. The number of neutrophils present influences the amount of tissue destructive components liberated. The migration (chemotaxis) of neutrophils as well as the ability of these leucocytes to liberate cytotoxic agents are therefore essential to the formation of pain and also to the degree of tissue destruction locally.

Eicosanoids of interest to neutrophile function are the leucotriens. Intake of fish oil may decease the production of leuotriens and inhibit neutrophil function. In that way fish oil may act as an anti-inflammatory agent.

In addition, fish-oil may inhibit the proliferation of another group of white blood cells, the lymphocytes as cytotoxic lymphocyte activity has been reported to be significantly diminished after intake of fish-oil.

Mechanisms behind the impact of fish oil on pain and stiffness in rheumatoid arthritis and osteoarthrosis therefore can be:
1) inhibition of the production of eicosanoids, e.g., leucotriens, which modify neutrophil function, and
2) inhibition of cell injury by inhibiting cytotoxic activity of neutrophils and lymphocytes.

Rose-hip powder was tested in vitro using a modified boyden chamber. After the addition of even low doses of rose-hip, neutrophil chemotaxis towards the chemotactic peptide f-Met-Leu-Phe and Zymosan was markedly reduced. Moreover, the oxidative burst from neutrophils, when using chemiluminescence, was abolished indicating antioxidative properties. When chemotaxis and oxidative burst response were tested in humans taking rose-hip powder, neutrophil chemotaxis and oxidative burst response significantly declined using even low concentrations of Rose-hip. It was also shown that in a small group of patients suffering from osteoarthrosis, pain significantly declined after four weeks of rose-hip treatment. This study was recently followed by a larger placebo-controlled double blind study on 100 patients with X-ray verified osteoarthrosis in which a significant decline in pain and stiffness of the hip joint was observed after four months of rose-hip therapy.

The basic mechanisms behind this reduction in pain and stiffness might well be the reduction in migration of neutrophils (resulting in a lessening of the amount of cytotoxicity liberated) and the reduction in neutrophil oxidative burst response, resulting in less cell destruction. A cell preserving capacity of rose-hip was also shown in a study on red cells which sustained more stress before membrane disintegrated, in human volunteers treated with rose-hip for four weeks.

As fish oil inhibits the production of eicosanoids such as prostaglandins, thromboxane and leucotrienes, it is likely to also inhibit platelet aggregation. Platelet aggregation was not inhibited when rose-hip was given to healthy volunteers, suggesting that the arachidonic acid pathway was not inhibited by rose-hip. It is therefore believed that the inhibitory effect of neutrophil chemotaxis observed using fish-oil and rose-hip have different pathways (fish oil use the arachidonic pathway and rose-hip use an alternative pathway not yet fully elucidated). The impact on migration of neutrophils might therefore be additive.

In addition, fish oil affect neutrophil and lymphocyte mediated cytotoxicity. Rose-hip has not been reported to interfere with lymphocyte function. However, rose hip exert strong antioxidative properties and rose-hip was reported to preserve cell membranes from disintegration.

Thus, rose-hip and fish-oil in combination are complimentary to each other and thus superior to fish-oil or rose-hip alone regarding the reduction of pain and stiffness in patients suffering from osteoarthrosis, as established by the above examples, and further may have prophalactic effects to prevent further disease progression.

These results are quite surprising particularly in view of the concentrations used. To treat inflammation as described in the '960 Patent, about 45 g were used on a daily basis as opposed to the 5 g per day utilized in the present combination. Fish oil is typically consumed at about 1 to 4 g per day and this is higher than the dosages that can be used in accordance with the present invention of about 0.1 to 0.8 g. Despite the significantly lower concentrations, a significantly greater beneficial result is obtained which reduces joint pain and joint stiffness, and these results are believed to not only treat the joint symptoms but in view of the likely pathways of action, can also be utilized as a prophylaxis for preventing or limiting progression of joint disease.

While preferred embodiments of the present invention have been shown and described, it will be understood by those skilled in the art that various changes or modifications can be made without varying from the scope of the present invention.

What is claimed is:

1. A formulation for alleviating symptoms associated with joint disease, joint pains and/or joint stiffness comprising a rose-hip concentrate and fish oil, the rose-hip and fish oil being in a ratio of about 20 to 1 to about 1.3 to 1 respectively.

2. The formulation of claim 1 further comprising a physiologically acceptable carrier.

3. The formulation of claim 1 wherein the formulation is in a unit dosage form.

4. The formulation of claim 1 wherein the rose-hip concentrate is present in an amount of from about 1.5 to about 30 g.

5. The formulation of claim 1 wherein the fish oil has about 0.1 to about 1.8 g of polyunsaturated fatty acids.

6. The formulation of claim 1 wherein the Rose-hip concentrate has a high vitamin C content.

7. The formulation of claim 1 wherein the Rose-hip concentrate and fish oil are present in a ratio of about 5 to 1 to about 1.6 to 1, respectively.

8. The formulation of claim 1 wherein the fish oil is in a powdered form.

9. The formulation of claim 1 wherein the fish oil is in a powdered form containing about 41 to 42.2 mg/g eicosapentaenoic acid as triglycerides and about 27 to 28.8 mg/g docosahexanoic acid as triglycerides.

10. The formulation of claim 1 wherein the fish oil is present at from about 0.5 to about 3.6 g.

11. The formulation of claim 1 wherein the formulation has from about 1300 to 2600 mg of fish oil and about 5 g of Rose-hip concentrate.

\* \* \* \* \*